(12) United States Patent
Thalappil et al.

(10) Patent No.: US 9,733,184 B2
(45) Date of Patent: Aug. 15, 2017

(54) VISUAL DETECTION OF MERCURY IONS

(75) Inventors: Pradeep Thalappil, Tamilnadu (IN);
Ammu Mathew, Kerala (IN);
Panikkanvalappil Ravindranathan Sajanlal, Kerala (IN)

(73) Assignee: Indian Institute of Technology Madras, Chennai (IN)

(*) Notice: Subject to any disclaimer, the term of this patent is extended or adjusted under 35 U.S.C. 154(b) by 28 days.

(21) Appl. No.: 14/389,702

(22) PCT Filed: Aug. 10, 2012

(86) PCT No.: PCT/IB2012/001543
§ 371 (c)(1),
(2), (4) Date: Sep. 30, 2014

(87) PCT Pub. No.: WO2013/144674
PCT Pub. Date: Oct. 3, 2013

(65) Prior Publication Data
US 2015/0053868 A1    Feb. 26, 2015

(30) Foreign Application Priority Data
Mar. 30, 2012 (IN) .......................... 1273/CHE/2012

(51) Int. Cl.
*H01J 65/08*    (2006.01)
*G01N 21/64*    (2006.01)
(Continued)

(52) U.S. Cl.
CPC .......... *G01N 21/6447* (2013.01); *B82Y 30/00* (2013.01); *G01N 21/643* (2013.01); *G01N 33/20* (2013.01); *G01N 2021/7786* (2013.01)

(58) Field of Classification Search
CPC ........ B82Y 30/00; B82Y 5/00; G01N 21/643; G01N 33/587; G01N 2021/6439;
(Continued)

(56) References Cited

U.S. PATENT DOCUMENTS 5,612,184 A    3/1997 Rosson
5,854,084 A *  12/1998 Drukier ............... C12Q 1/6816
                                                     435/7.1
(Continued)

FOREIGN PATENT DOCUMENTS

IN    3249CHE2008 A    7/2010
WO    2009045632 A2    4/2009

OTHER PUBLICATIONS

Author: Panikkanvalappil R. Sajanlal, Theruvakkattil S. Sreeprasad, Akshaya K. Samal and Thalappil Pradeep, Title:Anisotropic nanomaterials: structure, growth, assembly, and functions, Date:Feb. 16, 2011, Publisher: Nano Reviews 2011.*
(Continued)

*Primary Examiner* — David J Makiya
*Assistant Examiner* — Taeho Jo
(74) *Attorney, Agent, or Firm* — Pepper Hamilton LLP

(57) ABSTRACT

Composite materials comprising a mesoflower structure, methods of preparing the composite material, and methods of detecting heavy metal ion using the composite material are described herein. In some embodiments, a silica-coated gold mesoflower with a layer of silver quantum clusters may be capable of detecting $Hg^{2+}$ ions in a sample at zeptomolar concentrations.

29 Claims, 1 Drawing Sheet

(51) Int. Cl.
*B82Y 30/00* (2011.01)
*G01N 33/20* (2006.01)
*G01N 21/77* (2006.01)

(58) Field of Classification Search
CPC ....... G01N 2021/7786; G01N 21/6447; G01N 21/6456; G01N 33/20
USPC .................................................. 250/459.1
See application file for complete search history.

(56) References Cited

U.S. PATENT DOCUMENTS

| | | | |
|---|---|---|---|
| 6,436,259 B1 | 8/2002 | Russell | |
| 7,964,721 B2 | 6/2011 | Chang et al. | |
| 8,062,893 B2 | 11/2011 | Wang et al. | |
| 2005/0130188 A1* | 6/2005 | Walt | B01J 19/0046 506/3 |
| 2005/0171433 A1* | 8/2005 | Boppart | A61B 5/416 600/473 |
| 2005/0253983 A1* | 11/2005 | Carson | B82Y 20/00 349/97 |
| 2005/0272110 A1* | 12/2005 | Drukier | G01N 33/60 435/7.93 |
| 2006/0286684 A1* | 12/2006 | Brennan | B01J 13/0034 436/525 |
| 2007/0178534 A1* | 8/2007 | Murphy | B82Y 15/00 435/7.2 |
| 2008/0081376 A1 | 4/2008 | Harnandez et al. | |
| 2009/0022766 A1* | 1/2009 | Geddes | A61K 8/19 424/401 |
| 2009/0140206 A1* | 6/2009 | Nie | B82Y 30/00 252/301.16 |
| 2010/0230615 A1* | 9/2010 | MacPherson | B42D 25/364 250/488.1 |
| 2011/0043331 A1* | 2/2011 | Pradeep | B82Y 30/00 340/5.86 |
| 2011/0129537 A1* | 6/2011 | Vo-Dinh | A61K 41/0066 424/490 |
| 2011/0165689 A1* | 7/2011 | Ying | B82Y 5/00 436/81 |
| 2011/0200534 A1* | 8/2011 | Cheon | A61K 49/183 424/9.32 |
| 2011/0275061 A1* | 11/2011 | Weidemaier | G01N 21/658 435/6.1 |
| 2012/0329998 A1* | 12/2012 | Cui | G01N 33/582 530/391.5 |
| 2013/0017395 A1* | 1/2013 | Zhou | C09K 11/02 428/402.24 |

OTHER PUBLICATIONS

Author: Wei Wang and Hua Cui, Title: Chitosan-Luminol Reduced Gold Nanoflowers: From One-Pot Synthesis to Morphology-Dependent SPR and Chemiluminescence Sensing, Date:Jun. 27, 2008, Publisher: 2008 American Chemical Society.*
Author: DeeptiKrishnan,T.Pradeep, Title: Precursor-controlledsynthesisofhierarchicalZnOnanostructures,using oligoaniline-coated Au nanoparticleseeds, Date:2009, Publisher: 2009ElsevierB.V.*
Mathew et al., Molecular precursor-mediated tuning of gold mesostructures: Synthesis and SERRS studies, *Journal of Crystal Growth* (Dec. 3, 2009), 312:587-594.
Search report for Chinese counterpart application No. CN 2012800735327.
International Search Report and Written Opinion for PCT/IB2012/001543 dated Feb. 15, 2013.
Aragay et al., Recent Trends in Macro-, Micro-, and Nanomaterial-Based Tools and Strategies for Heavy-Metal Detection, *Chem. Rev.* (2011), 111:3433-3458.
Caballero et al., Highly Selective Chomogenic and Redox of Fluorescent Sensors of $Hg^{2+}$ in Aqueous Environment Based on 1,4-Disubstitued Azines, *J. Am. Chem. Soc.* (2005), 127:15666-15667.
Gong et al., Stripping Voltammetric Detection of Mercury(II) Based on a Bimetallic Au—Pt Inorganic-Organic Hybrid Nanocomposite Modified Glassy Carbon Electrode, *Anal. Chem.* (Jan. 15, 2010), 82(2):567-573.
Guerrero et al., Surface-Enhanced Fluorescence with Shell-Isolated Nanoparticles (SHINEF), *Angew. Chem. Int. Ed.* (2011), 50:665-668.
Huang et al., Synthesis of Highly Fluorescent Gold Nanoparticles for Sensing Mercury(II), *Angew. Chem. Int. Ed.* (2007), 46:6824-6828.
Mutter et al., Comments on the Article "The Toxicology of Mercury and Its Chemical Compounds" by Clarkson and Magos (2006), *Critical Reviews in Toxicology* (2007), 37:537-549.
Selid et al., Sensing Mercury for Biomedical and Environmental Monitoring, *Sensors* (Jul. 9, 2009), 9:5446-5459.
Song et al.; Picomolar selective detection of mercuric ion ($Hg^{2+}$) using a functionalized single Plasmonic gold nanoparticle, *Nanotechnology* (Mar. 10, 2010), 21:145501:1-145501:6.
Wang et al., Gold Nanoparticle-Based Coloimetric and "Turn-On" Fluorescent Probe for Mercury(II) Ions in Aqueous Solution, *Anal. Chem.* (Dec. 1, 1998), 80(23):9021-9028.
Bootharaju and Pradeep, Investigation into the Reactivity of Unsupported and Supported Ag7 and Ag8 Clusters with Toxic Metal Ions, Langmuir (Jun. 13, 2011), 27(13) pp. 8134-8143.
Bootharaju and Pradeep, Uptake of Toxic Metal Ions from Water by Naked and Monolayer Protected Silver Nanoparticles: An X-ray Photoelectron Spectroscopic Investigation, The Journal of Physical Chemistry C (Apr. 15, 2010), (114) 8328-8336.
Clarkson and Magos, The toxicology of mercury and its chemical compounds, Critical Reviews in Toxicology (Sep. 2006), 36(8) pp. 609-662.
Darbha et al., Gold Nanoparticle-Based Miniaturized Nanomaterial Surface Energy Transfer Probe for Rapid and Ultrasensitive Detection of Mercury in Soil, Water, and Fish, ACS NANO (Oct. 31, 2007) 1(3) pp. 208-214.
Mathew et al., A fifteen atom silver cluster confined in bovine serum albumin, Journal of Materials Chemistry (Jun. 23, 2011), (21) pp. 11205-11212.
Pradeep et al., Towards a practical solution for removing inorganic mercury from drinking water using gold nanoparticles, Gold Bulletin (2009), 42(2) 144-152.
Sajanlal, Functional Mesoflowers: A New Class of Materials for Molecular Sensing, Chennai Chemistry Conference, IIT (Feb. 17, 2011), pp. 1-8.
Sajanlal and Pradeep, Mesoflowers: A New Class of Highly Efficient Surface-Enhanced Raman Active and Infrared-Absorbing Materials, Nano Research (Feb. 5, 2009), (2) pp. 306-320.
Sajanlal et al., Wires, Plates, Flowers, Needles, and Core-Shells: Diverse Nanostructures of Gold Using Polyaniline Templates, Langmuir (May 6, 2008), 24(9) pp. 4607-4614.
Song et al, Picomolar selective detection of mercuric ion (Hg2 +) using a functionalized single plasmonic gold nanoparticle, Nanotechnology (Mar. 10, 2010), 21(14) pp. 145501-145506.
Sumesh et al., A practical silver nanoparticle-based adsorbent for the removal of Hg2+ from water, Journal of Hazardous Materials (May 15, 2011), 189(1-2) pp. 450-457.
Wang et al., Gold Nanoparticle-Based Colorimetric and 'Turn-On' Fluorescent Probe for Mercury (II) Ions in Aqueous Solution, Anal. Chem. (Oct. 31, 2008), 80(23) pp. 9021-9028.

* cited by examiner

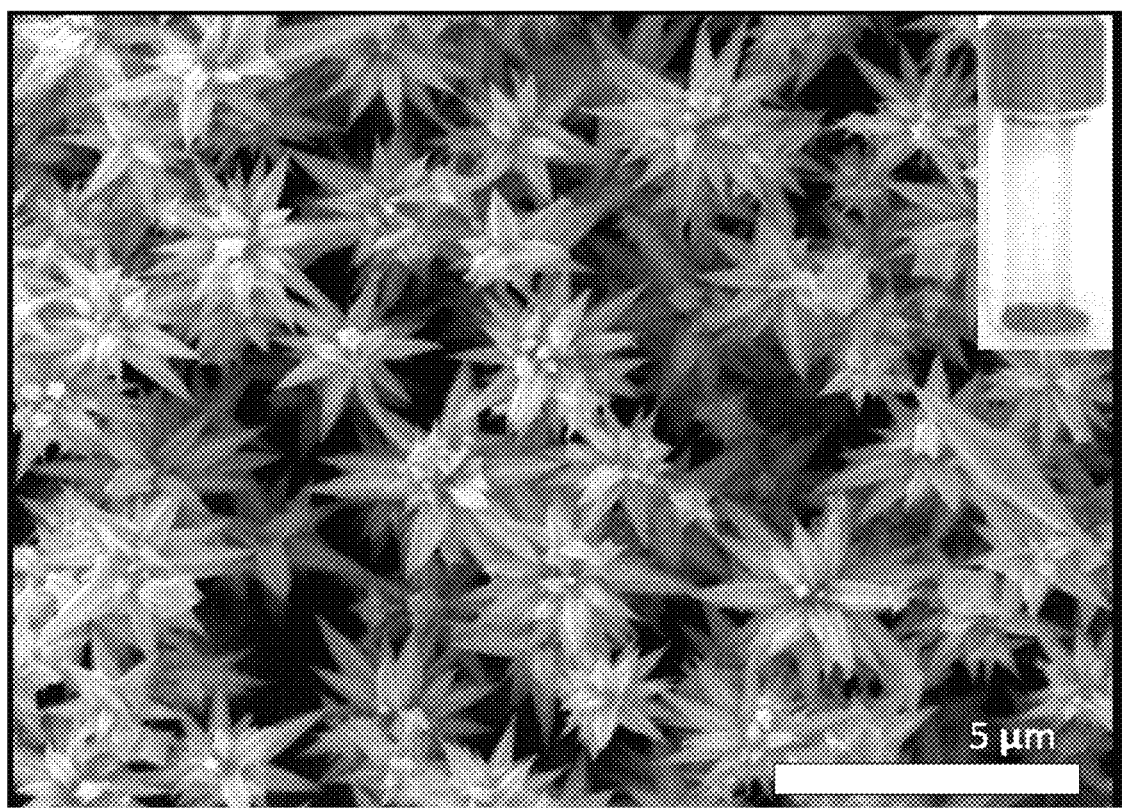

VISUAL DETECTION OF MERCURY IONS

CLAIM OF PRIORITY

This application is a U.S. national stage filing under 35 U.S.C. §371 of International Application No. PCT/IB2012/001543, filed Aug. 10, 2012, which claims priority to Indian Application No. 1273/CHE/2012, filed Mar. 30, 2012, and entitled "Visual Detection of Mercury Ions," respectively, the disclosure of which is incorporated by reference in its entirety.

BACKGROUND

Heavy metal ions have numerous adverse health effects due to their eco-toxic, carcinogenic and non-biodegradable nature. Detection of heavy metals using nanoparticle based sensors are typically based on monitoring changes in the properties of the nanoparticles, such as changes in surface plasmon resonance (SPR) absorptions, fluorescence, inter-nanoparticle interactions (ion-chelation-induced aggregation process), and others, upon binding of an analyte. These changes may be detected using absorption and fluorescence spectroscopy; however, they often require relatively larger sensor and analyte concentrations and may have anomalies due to ensemble averaging. Integration of chemosensors into a single particle sensory device would be an ideal prospect, as it increases the sensitivity of detection. Single particle sensors employed so far have disadvantages owing to difficulty in locating and distinguishing such particles with other impurities in the system as they may not have a unique shape. The limits of such detection systems have not extended beyond the femtomolar regime.

SUMMARY

This disclosure is not limited to the particular systems, devices and methods described, as these may vary. The terminology used in the description is for the purpose of describing the particular versions or embodiments only, and is not intended to limit the scope. While various compositions and methods are described in terms of "comprising" various components or steps (interpreted as meaning "including, but not limited to"), the compositions and methods can also "consist essentially of" or "consist of" the various components and steps, and such terminology should be interpreted as defining essentially closed-member groups.

Presently disclosed are metallic composite materials, methods of making the composite materials, and methods of detecting mercury ions at a very low concentration using the composite materials in a single particle-based detection approach. The methods described herein may be used for ultra-trace sensitivity detection of mercury ions.

Embodiments describe metallic composite materials comprising a mesoflower structure having a metal core and a plurality of luminescent nanoparticles affixed to the mesoflower structure, wherein the composite material has an observable luminescent emission when heavy metal ions are not bound to the composite material and the emission changes when heavy metal ions are bound to the composite material.

Embodiments describe methods of preparing a metallic composite material comprising: providing a mesoflower structure having a metal core; contacting the mesoflower structure with a mixture comprising a silane to produce a mixture comprising a silicon dioxide coated mesoflower structure; isolating the silicon dioxide coated mesoflower structure; providing a plurality of luminescent nanoparticles; and contacting the silicon dioxide coated mesoflower structure with the plurality of luminescent nanoparticles to produce a mixture comprising the composite material.

Embodiments describe methods of detecting heavy metal ions in a sample comprising: providing a metallic composite material; contacting the composite material with a sample containing, or suspected of containing, heavy metal ions; exposing the composite material to light comprising at least one wavelength capable of exciting the composite structure; and detecting the observable luminescent emission of the composite material, wherein a change in the observable luminescent emission of the composite material following contact with the sample indicates that heavy metal ions are bound to the composite material and that heavy metal ions are present in the sample.

Embodiments describe kits useful for detection of heavy metal ions, wherein the kit comprises a metallic composite material comprising a mesoflower structure having a metal core and a plurality of luminescent nanoparticles affixed to the mesoflower structure and at least one secondary reagent or reaction container.

DESCRIPTION OF FIGURE

The FIGURE is a transmission electron micrograph of gold mesoflowers in accordance with an embodiment.

DETAILED DESCRIPTION

Described herein are metallic composite materials, methods of making the composite materials, and methods of detecting mercury ions at a very low concentration using the composite materials in a single particle-based detection approach. In some embodiments, the composite material may be a composite material made of gold mesoflowers and silver quantum clusters.

In embodiments, a metallic composite material made by functionalizing gold mesoflowers with silver quantum clusters may be used in sensing applications in new and more sensitive formats. Detection of mercury ions may be achieved at a very low concentration (zeptomoles) using these methods. The methods described herein may provide a highly selective and sensitive way to recognize the presence of mercury ions in a mixture, well beyond the detection limit compared to conventional solution based approaches, by monitoring changes in the fluorescence of the composite material. In further embodiments, a turn-on sensor may be prepared by providing an additional functionality in the form of a fluorophore to the composite material. In embodiments, only a single particle may be required for the detection of an analyte.

In the following embodiments, a mesoflower may be unsymmetrical at the single particle level resembling natural objects, such as flowers, starfish, or sea urchins, and may comprise of a large number of stems with unusual pentagonal symmetry (the FIGURE). Mesoflowers may have a high degree of structural purity with star-shaped, nano-structured stems. In embodiments, mesoflowers may be obtained in high yield, essentially free of contaminating structures and its size may be tuned from nano- to meso-dimensions. In the following embodiments, a mesoflower structure may have a size of about 500 nm to about 10 μm. In some embodiments, a mesoflower structure may have a size of about 500 nm, about 1 μm, about 1.5 μm, about 2 μm, about 2.5 μm, about 3 μm, about 4 μm, about 5 μm, about 6 μm, about 8 μm, or about 10 μm. Specific examples of sizes include about 500 nm, about 1 µm, about 2 µm, about 3 µm, about 4 µm, about 4.5 µm, about 6 µm, about 10 µm, and ranges between any two of these sizes (for example, about 4 µm to about 10 µm).

In the following embodiments, a mesoflower structure may have a metal core. The metal core may be mono-metallic, bi-metallic, or tri-metallic. In some embodiments, the metal core may comprise gold. In these embodiments, the metal core may comprise a layer of silver, nickel, cobalt, platinum, or a combination thereof. In further embodiments, the metal core may comprise an additional layer of nickel, cobalt, or a combination thereof. For example, a bi-metallic metal core may be gold coated with silver, and a tri-metallic metal core may be gold coated with platinum coated with nickel.

In the following embodiments, luminescent nanoparticles may comprise quantum clusters. In some embodiments, the quantum clusters may comprise $Au_{25}$, $Au_{18}$, or $Ag_{15}$ clusters confined in bovine serum albumin or glutathione. In some embodiments, the quantum clusters may comprise $Ag_{15}$ clusters confined in bovine serum albumin. In these embodiments, a composite material comprising the luminescent nanoparticles may exhibit red luminescent emission when illuminated with light of a wavelength of about 490 nanometers and heavy metal ions are not bound to the composite material.

In the following embodiments, a fluorescent dye may be selected from known organic and organometallic fluorophores. Common generic fluorescent dye families may include Xanthene derivatives (e.g., fluorescein, rhodamine, OREGON GREEN, eosin, TEXAS RED, CAL FLUOR dyes, eosines, phloxines, uranines, succineins, sacchareins, rosamines, rhodols, pyranines, anthraquinones, benzopyrans, thioxanthenes, perylene imides, phenanthridines, carbopyronins, and fluorescent proteins such as green fluorescent protein and yellow fluorescent protein); Cyanine derivatives (e.g., cyanine, indocarbocyanine, oxacarbocyanine, thiacarbocyanine, merocyanine, and QUASAR dyes); Naphthalene derivatives (e.g., dansyl and prodan derivatives); Coumarin derivatives; Oxadiazole derivatives (e.g., pyridyloxazole, nitrobenzoxadiazole and benzoxadiazole); Pyrene derivatives (e.g., CASCADE BLUE, etc.); Oxazine derivatives (e.g., Nile red, Nile blue, cresyl violet, oxazine 170, etc.); Acridine derivatives (e.g., proflavin, acridine orange, acridine yellow, etc.); Arylmethine derivatives (e.g., auramine, crystal violet, malachite green); and Tetrapyrrole derivatives (e.g., porphin, phthalocyanine, bilirubin), among others. Common proprietary/trademarked fluorescent dye families may include CYDYE (GE Healthcare); CF dye (Biotium); BODIPY (Invitrogen); ALEXA FLUOR (Invitrogen); DYLIGHT FLUOR (Thermo Scientific, Pierce); ATTO and TRACY (Sigma Aldrich); FLUOPROBES (Interchim); MEGASTOKES Dyes (Dyomics); SETA Dyes (SETA BioMedicals); SETAU Dyes (SETA BioMedicals); and SQUARE Dyes (SETA BioMedicals), among others. In some embodiments, a fluorescent dye may be selected from derivatives of naphthalene, xanthene, pyrene, and acridine. In these embodiments, the fluorescent dye may be fluorescein isothiocyanate.

In an embodiment, a method of preparing a metallic composite material may comprise: providing a mesoflower structure having a metal core; contacting the mesoflower structure with a solution comprising tetraethyl orthosilicate or (3-aminopropyl)trimethoxysilane to produce a mixture comprising a silicon dioxide coated mesoflower structure; isolating the silicon dioxide coated mesoflower structure; providing a plurality of luminescent nanoparticles; and contacting the silicon dioxide coated mesoflower structure with the plurality of luminescent nanoparticles to produce a mixture comprising the composite material. In some embodiments, the method may further comprise centrifuging the mixture comprising the composite material to produce a residue comprising the composite material and adding water to the residue comprising the composite material to produce a mixture comprising purified composite material. In these embodiments, the method further may comprise repeating the centrifuging and adding water steps one to five times to produce a mixture consisting essentially of the composite material.

In some embodiments, isolating the silicon dioxide coated mesoflower structure may comprise centrifuging the mixture comprising the silicon dioxide coated mesoflower structure and decanting to produce a residue comprising the silicon dioxide coated mesoflower structure. In these embodiments, isolating the silicon dioxide coated mesoflower structure may further comprise adding water to the residue comprising the silicon dioxide coated mesoflower structure and repeating the centrifuging and decanting steps one to five times to produce a residue comprising a substantially pure silicon dioxide coated mesoflower structure.

In some embodiments, the solution comprising tetraethyl orthosilicate or (3-aminopropyl)trimethoxysilane further may comprise a fluorescent dye. In some embodiments, the fluorescent dye may be fluorescein isothiocyanate.

In an embodiment, a metallic composite material useful for the detection of heavy metal ions may comprise a mesoflower structure having a metal core and a plurality of luminescent nanoparticles affixed to the mesoflower structure. In embodiments, the composite material may have an observable luminescent emission when heavy metal atoms are not bound to the composite material, and the observable luminescent emission may change when heavy metal atoms are bound to the composite material. In embodiments, the change in the observable luminescent emission may be a shift to a different wavelength, a diminished intensity, an intensified intensity, or a combination thereof.

In some embodiments, the plurality of luminescent nanoparticles may be separated from the metal core by at least one inert layer. In these embodiments, the at least one inert layer may comprise a metal oxide. In some embodiments, the at least one inert layer may comprise aluminum oxide, titanium dioxide, zirconium oxide, silicon dioxide, or a combination thereof. In some embodiments, the at least one inert layer may comprise silicon dioxide.

In embodiments, the heavy metal ions may be selected from the group consisting of mercury, lead, nickel, arsenic, aluminum, cobalt, chromium, manganese, copper, cadmium, and combinations thereof. In some embodiments, the heavy metal ions may be mercury, copper, or a combination thereof. In some embodiments, the heavy metal ions may be mercury ions and they may be selectively bound by the composite material relative to other heavy metal ions. In some embodiments, the observable luminescent emission may have a diminished intensity when heavy metal atoms are bound to the composite material.

In further embodiments, the at least one inert layer may comprise a fluorescent dye. In some embodiments, the fluorescent dye may be fluorescein isothiocyanate. In these embodiments, the observable luminescent emission may have a shifted wavelength when heavy metal atoms are bound to the composite material.

As used herein, "sensitivity" is intended to define the ability to perceive a change in the observable luminescent emission due to heavy metal atoms binding to the composite material when the composite material is contacted with a sample containing an amount of heavy metal ions. In some embodiments, the change in the observable luminescent emission may have sensitivity to heavy metal ions at a concentration of about 0.1 zeptomolar to about 100 femtomolar. Specific examples of concentrations are about 0.1 zeptomolar, about 1 zeptomolar, about 10 zeptomolar, about 100 zeptomolar, about 1 attomolar, about 10 attomolar, about 100 attomolar, about 1 femtomolar, about 10 femtomolar, about 100 femtomolar, and any concentration or range of concentrations between those listed (for example, about 0.1 zeptomolar to about 10 attomolar). In some embodiments, the change in the observable luminescent emission may have sensitivity to heavy metal ions at a concentration of about 0.1 zeptomolar. In some embodiments, heavy metal ions may be within a test sample. In these embodiments, the sample may be a water sample or a biological sample (e.g., blood, urine, mucus, or tissue).

In an embodiment, a method of detecting heavy metal ions in a sample comprises: providing a metallic composite material described in the embodiments above; contacting the composite material with a sample containing, or suspected of containing, heavy metal ions; exposing the composite material to light comprising at least one wavelength capable of exciting the composite structure; and detecting the observable luminescent emission of the composite material. In embodiments, a change in the observable luminescent emission of the composite material following contact with the sample indicates that heavy metal ions are bound to the composite material and that heavy metal ions are present in the sample.

In some embodiments, providing a composite material may comprise making a mixture comprising the composite material. In these embodiments, contacting the composite material with a sample containing, or suspected of containing, heavy metal ions may comprise adding the sample containing, or suspected of containing, heavy metal ions to the mixture comprising the composite material. In other embodiments, providing a composite material may comprise making a drop-cast film of the composite material. In these embodiments, contacting the composite material with a sample containing, or suspected of containing, heavy metal ions may comprise adding the sample containing, or suspected of containing, heavy metal ions to the drop-cast film of the composite material.

In embodiments, the sample containing, or suspected of containing, heavy metal ions may be a water sample or a biological sample. In some embodiments, the heavy metal ions may be selected from the group consisting of chromium, zinc, silver, selenium, thorium, uranium, manganese, mercury, lead, nickel, arsenic, aluminum, cobalt, magnesium, copper, cadmium, and combinations thereof. In some embodiments, the heavy metal ions may be mercury, copper, or a combination thereof. Specific examples of heavy metal ions include, but are not limited to: $Cr^{6+}$, $Zn^{2+}$, $Ag^+$, $Se^{2+}$, $Th^{4+}$, $U^{6+}$, $Mn^{2+}$, $Co^{2+}$, $Hg^{2+}$, $Pb^{2+}$, $Ni^{2+}$, $Cd^{2+}$, $Mg^{2+}$, and $Cu^{2+}$. In some embodiments, the heavy metal ions may be mercury ions and the mercury ions may be selectively detected from other heavy metal ions.

In some embodiments, the change in the observable luminescent emission of the composite material following contact with the sample may have a magnitude proportional to the amount of heavy metal in the sample. In embodiments, the sample containing, or suspected of containing, heavy metal ions contains heavy metal ions at a femtomolar, attomolar, or zeptomolar concentration, and the change in the observable luminescent emission of the composite material following contact with the sample may be observable. In embodiments, the sample containing, or suspected of containing, heavy metal ions contains heavy metal ions at a concentration of at least about 0.1 zeptomolar, and the change in the observable luminescent emission of the composite material following contact with the sample may be observable.

In an embodiment, a kit useful for detection of heavy metal ions comprises: a metallic composite material comprising a mesoflower structure having a metal core and a plurality of luminescent nanoparticles affixed to the mesoflower structure, wherein the composite material has an observable luminescent emission when heavy metal ions are not bound to the composite material and there is a change in the observable luminescent emission when heavy metal ions are bound to the composite material; and at least one secondary reagent or reaction container.

EXAMPLES

Example 1: Synthesis of Au/Oligoaniline Nanoparticles

Citric acid (25 mg) of was dissolved in 35 mL of distilled water and maintained at 80° C. To this solution was added 1 mL of 25 mmol/L $HAuCl_4$. After the color changed from pale yellow to pink, 100 µL distilled aniline was added immediately followed by 500 µL of 25 mmol/L $HAuCl_4$ and heating was continued for 5 more min. The mixture cooled to room temperature. The mixture was kept at room temperature for 5 h and then centrifuged at 4000 rpm. The light pink supernatant, containing Au/oligoaniline nanoparticles, was collected and used for further reactions. Au/oligoaniline nanoparticles are raspberry-like aggregates of small nanoparticles (~3 nm diameter), forming 75-100 nm structures, which are embedded in an oligoaniline matrix.

Example 2: Synthesis of Silica Coated Gold Mesoflowers

To a 20 mL CTAB solution (100 mM) in a beaker, 335 µL $HAuC_{14}$ (25 mM), 125 µL $AgNO_3$ (10 mM) and 135 µL ascorbic acid (100 mM) were added sequentially. To this solution, 2 mL of the Au/oligoaniline nanoparticles from Example 1 were added, and the mixture was maintained at 80° C. for 1 hour. It was then cooled to room temperature and the mixture was centrifuged at 3500 rpm for 4 minutes. The residue containing gold mesoflowers was washed with water three times in order to remove excess CTAB and other unwanted materials. The gold mesoflowers were dispersed in isopropanol (2 mg in 10 mL). Tetraethyl orthosilicate TEOS (120 µL) and ammonia (1.5 mL) solutions were added under rapid stirring. The mixture was centrifuged and the supernatant was removed to arrest self nucleation of silica particles. The residue was cleaned a couple of times by centrifugation and redispersed in water/isopropanol. This yielded a uniform coating of silica (approximately 25 nm) on the gold mesoflowers.

Example 3: Synthesis of $Ag_{15}$ Quantum Clusters Confined in Bovine Serum Albumin A silver nitrate solution (5 mL at 10 mM) was added to bovine serum albumin powder in distilled water (250 mg in 5 mL) with vigorous stirring at room temperature. About 0.3 mL NaOH (1 M) was added, followed by drop-wise addition of a 10 mM $NaBH_4$ solution until the solution turned from colorless to reddish brown (about 120 μL); indicating the formation of $Ag_{15}$ quantum clusters confined in bovine serum albumin.

Example 4: Synthesis of Silica Coated Gold Mesoflowers Loaded with $Ag_{15}$ Quantum Clusters Confined in Bovine Serum Albumin Gold mesoflowers from Example 1 were dispersed in distilled water, and (3-aminopropyl)trimethoxysilane (APTMS) was added. The mixture was kept for 15 minutes and centrifuged. To the residue, a mixture containing $Ag_{15}$ quantum clusters confined in bovine serum albumin, from Example 2, was added and incubated for 30 minutes. The mixture was again centrifuged and the residue was washed with water, this process was repeated three times to ensure the removal of unbound quantum cluster from the mixture. Attachment of silver clusters to the surface of the gold mesoflowers was verified using energy-dispersive X-ray spectroscopy (EDAX).

Example 5: Detection of Heavy Metal Ions Using Silica Coated Gold Mesoflowers Loaded with $Ag_{15}$ Quantum Clusters Confined in Bovine Serum Albumin A batch of mesoflowers from Example 3 were drop casted on to a glass slide, and one drop of each metal ion solution ($Hg^{2+}$, $Pb^{2+}$, $Ni^{2+}$, $Cd^{2+}$, and $Cu^{2+}$) was added separately, dried, and monitored under a fluorescence microscope (CytoViva). Fluorescence images (490 nm excitation) of metal ion-treated gold mesoflowers were compared with untreated gold mesoflowers. Quenching of cluster luminescence was more pronounced in the case of $Cu^{2+}$ and $Hg^{2+}$ ions than for the other ions at 100 ppm each. A feeble luminescence pattern was observed in case of $Cu^{2+}$ ions (10 ppm), but $Hg^{2+}$ ions (10 ppm) resulted in complete quenching of cluster luminescence.

In order to check the lower detection limit, experiments using 10 ppb, 500 ppt and 10 ppt of $Hg^{2+}$ ions were conducted. While a concentration of 10 ppb of $Hg^{2+}$ ions showed complete quenching of cluster luminescence, a substantial quenching was also observed for 500 ppt $Hg^{2+}$ ions. A slight decrease in fluorescence intensity was also noted for 10 ppt $Hg^{2+}$ ions.

In the 500 ppt example, 2.5 μL of a 500 ppt mercury solution was used to wet the gold mesoflowers. A large gold mesoflower of 4 μm length has a volume of about 34 femtoliters and that volume of 500 ppt solution contains about 50 $Hg^{2+}$ ions (or $0.083*10^{-21}$ moles). Thus, about 0.1 zeptomoles of $Hg^{2+}$ ions are being detected. The success of this sensing methodology lies in the nanostructures which enhance the sensitivity and the specificity of the protein protected quantum clusters to the analyte.

Example 6: Synthesis of Fluorescent Silica Coated Gold Mesoflowers

To a 20 mL CTAB solution (100 mM) in a beaker, 335 μL $HAuC_{14}$ (25 mM), 125 μL $AgNO_3$ (10 mM) and 135 μL ascorbic acid (100 mM) were added sequentially. To this solution, 2 mL of the Au/oligoaniline nanoparticles from Example 1 were added, and the mixture was maintained at 80° C. for 1 hour. It was then cooled to room temperature and the mixture was centrifuged at 3500 rpm for 4 minutes. The residue containing gold mesoflowers was washed with water three times in order to remove excess CTAB and other unwanted materials. The gold mesoflowers were dispersed in isopropanol (2 mg in 10 mL). Tetraethyl orthosilicate TEOS (120 μL), ammonia (1.5 mL), and fluorescein isothiocyanate (1 mL at 25 mM) solutions were added under rapid stirring. The mixture was centrifuged and the supernatant was removed to arrest self nucleation of silica particles. The residue was cleaned a couple of times by centrifugation and redispersed in water/isopropanol. This yielded a uniform coating of fluorescent silica (approximately 25 nm) on the gold mesoflowers which showed green luminescence under 490 nm excitation. Similar to Example 3, these mesoflowers were loaded with $Ag_{15}$ quantum clusters confined in bovine serum albumin. These loaded mesoflowers showed red luminescence under 490 nm excitation.

Example 7: Detection of Heavy Metal Ions Using Fluorescent Silica Coated Sold Mesoflowers Loaded with $Ag_{15}$ Quantum Clusters Confined in Bovine Serum Albumin Similar to Example 4, fluorescent silica coated gold mesoflowers loaded with $Ag_{15}$ quantum clusters confined in bovine serum albumin were drop cast and expose to heavy metal ions. In presence of $Hg^{2+}$ ions (1 ppb) the red luminescence of the cluster was completely quenched and the gold mesoflowers appeared green under 490 nm excitation due to the underlying fluorescein incorporated silica layer. Whereas, for the Gold mesoflowers treated with 500 ppt of $Hg^{2+}$ ions, the luminescence from the gold mesoflowers changed from red to yellowish orange. The yellow color observed may be due to the additive effect of the unquenched red luminescent cluster on the gold mesoflower surface and the underlying green luminescent fluorescein functionalised silica shell. This easily observable color change (red to green) in presence of $Hg^{2+}$ ions in solution enables ppt level detection of such ions.

In the present disclosure, reference is made to the accompanying FIGURE, which forms a part hereof. The illustrative embodiments described in the detailed description, the FIGURE, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURE, may be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or the FIGURE, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

We claim:

1. A metallic composite material comprising a mesoflower structure having a metal core and a plurality of luminescent nanoparticles affixed to the mesoflower structure, wherein:
    the composite material has a first luminescent emission when heavy metal ions are not bound to the composite material;
    the composite material has a second luminescent emission when the heavy metal ions are bound to the composite material, wherein the second luminescent emission is different from the first luminescent emission; and
    a delta of luminescent emission between the first luminescent emission and the second luminescent emission is observable in the heavy metal ions at a concentration of about 100 femtomolar to about 0.1 zeptomolar.

2. The composite material of claim 1, wherein the metal core comprises gold.

3. The composite material of claim 2, wherein:
    the metal core further comprises a layer of silver, nickel, cobalt, platinum, or a combination thereof.

4. The composite material of claim 1, wherein the plurality of luminescent nanoparticles is separated from the metal core by at least one inert layer.

5. The composite material of claim 4, wherein the at least one inert layer comprises aluminum oxide, titanium dioxide, zirconium oxide, silicon dioxide, or a combination thereof.

6. The composite material of claim 4, wherein the at least one inert layer further comprises a fluorescent dye.

7. The composite material of claim 6, wherein:
    the fluorescent dye is selected from fluorescein isothiocyanate and derivatives of naphthalene, xanthene, pyrene, and acridine; and
    the change in the luminescent emission when the heavy metal ions are bound to the composite material is a shift to a different wavelength.

8. The composite material of claim 1, wherein the plurality of luminescent nanoparticles comprise quantum clusters of at least one of $Au_{25}$ clusters, $Au_{18}$ clusters, or $Ag_{15}$ clusters.

9. The composite material of claim 8, wherein the quantum clusters comprise $Ag_{15}$ clusters confined in bovine serum albumin, and the composite material exhibits red luminescent emission when illuminated with light of a wavelength of about 490 nanometers and the heavy metal ions are not bound to the composite material.

10. The composite material of claim 1, wherein:
    the change in the luminescent emission has a sensitivity to the heavy metal ions at a concentration of about 0.1 zeptomolar; and the change in the luminescent emission is a shift to a different wavelength, a diminished intensity, an intensified intensity, or a combination thereof.

11. The composite material of claim 1, wherein:
the mesoflower structure has a dimension of about 500 nm to about 4 µm;
the heavy metal ions are selected from the group consisting of mercury, lead, nickel, arsenic, aluminum, cobalt, chromium, manganese, copper, cadmium, and combinations thereof;
the heavy metal ions selectively bound by the composite material are selectively bound relative to other heavy metal ions; and
the change in the luminescent emission when the heavy metal ions are bound to the composite material is a diminished intensity.

12. A method of preparing a metallic composite material, the method comprising:
providing a mesoflower structure having a metal core;
contacting the mesoflower structure with a solution comprising tetraethyl orthosilicate or (3-aminopropyl) trimethoxysilane to produce a solution comprising a silicon dioxide coated mesoflower structure;
isolating the silicon dioxide coated mesoflower structure;
providing a plurality of luminescent nanoparticles; and
contacting the silicon dioxide coated mesoflower structure with the plurality of luminescent nanoparticles to produce a solution comprising the composite material, wherein the composite material permits heavy metal ion detection at a concentration of about 100 femtomolar to about 0.1 zeptomolar.

13. The method of claim 12, wherein:
the metal core comprises gold coated with a layer of silver, nickel, cobalt, platinum, or a combination thereof; and
the plurality of luminescent nanoparticles comprise quantum clusters of at least one of $Au_{25}$ clusters, $Au_{18}$ clusters, or $Ag_{15}$ clusters.

14. The method of claim 13, wherein the composite material comprises $Ag_{15}$ clusters confined in bovine serum albumin and exhibits red luminescent emission when illuminated with light of a wavelength of about 490 nanometers.

15. The method of claim 12, wherein the solution comprising tetraethyl orthosilicate or (3-aminopropyl)trimethoxysilane further comprises a fluorescent dye.

16. The composite material of claim 15, wherein the fluorescent dye is selected from fluorescein isothiocyanate and derivatives of naphthalene, xanthene, pyrene, and acridine.

17. The method of claim 12, wherein isolating the silicon dioxide coated mesoflower structure comprises:
centrifuging the solution comprising the silicon dioxide coated mesoflower structure;
decanting to produce a residue comprising the silicon dioxide coated mesoflower structure;
adding water to the residue comprising the silicon dioxide coated mesoflower structure; and
repeating the centrifuging and decanting steps one to five times to produce a residue comprising a substantially pure silicon dioxide coated mesoflower structure having a dimension that is about 500 nm to about 2 µm.

18. A method of detecting heavy metal ions in a sample, the method comprising:
providing a metallic composite material, wherein the composite material comprises a mesoflower structure having a metal core and a plurality of luminescent nanoparticles affixed to the mesoflower structure, and wherein the composite material has a first luminescent emission when the heavy metal ions are not bound to the composite material;
contacting the composite material with the sample containing, or suspected of containing, the heavy metal ions;
exposing the composite material to light comprising at least one wavelength capable of exciting the mesoflower structure to produce a second luminescent emission; and
measuring the second luminescent emission of the composite material, wherein a second luminescent emission different from the first luminescent emission following contact with the sample indicates that the heavy metal ions are bound to the composite material and that the heavy metal ions are present in the sample, wherein a delta of luminescent emission between the first luminescent emission and the second luminescent emission is observable in the heavy metal ions at a concentration of about 100 femtomolar to about 0.1 zeptomolar.

19. The method of claim 18, wherein:
providing a composite material comprises making a solution comprising the composite material; and
contacting the composite material with the sample containing, or suspected of containing, the heavy metal ions comprises adding the sample containing, or suspected of containing, the heavy metal ions to the solution comprising the composite material.

20. The method of claim 18, wherein:
providing the composite material comprises making a drop-cast film of the composite material; and
contacting the composite material with the sample containing, or suspected of containing, the heavy metal ions comprises adding the sample containing, or suspected of containing, the heavy metal ions to the drop-cast film of the composite material.

21. The method of claim 18, wherein the metal core comprises gold optionally coated with a layer of silver, nickel, cobalt, platinum, or a combination thereof.

22. The method of claim 18, wherein the plurality of luminescent nanoparticles is separated from the mesoflower structure by at least one inert metal oxide layer.

23. The composite material of claim 22, wherein the at least one inert layer comprises aluminum oxide, titanium dioxide, zirconium oxide, silicon dioxide, or a combination thereof.

24. The method of claim 22, wherein:
the at least one inert layer further comprises a fluorescent dye selected from fluorescein isothiocyanate and derivatives of naphthalene, xanthene, pyrene, and acridine; and
the change in the luminescent emission is a shift to a different wavelength.

25. The method of claim 18, wherein the plurality of luminescent nanoparticles comprise quantum clusters of at least one of $Au_{25}$ clusters, $Au_{18}$ clusters, or $Ag_{15}$ clusters confined in bovine serum albumin or glutathione.

26. The method of claim 18, wherein:
the composite material exhibits red luminescent emission when illuminated with light of a wavelength of about 490 nanometers; and
the change in the luminescent emission is a shift to a different wavelength, a diminished intensity, an intensified intensity, or a combination thereof.

27. The method of claim 18, wherein the heavy metal ions are selected from the group consisting of mercury, lead, nickel, arsenic, aluminum, cobalt, chromium, manganese, copper, cadmium, and combinations thereof.

28. The method of claim 18, wherein:
the heavy metal ions are mercury ions and wherein the mercury ions are selectively detected from other heavy metal ions; and
the change in the luminescent emission is a diminished intensity.

29. The method of claim 18, wherein the method is a method for detecting the heavy metal ions at a femtomolar, attomolar, or zeptomolar concentration, and the sample containing, or suspected of containing, the heavy metal ions contains the heavy metal ions at a femtomolar, attomolar, or zeptomolar concentration, and the change in the luminescent emission of the composite material following contact with the sample has a magnitude proportional to an amount of heavy metal in the sample.

* * * * *